(12) United States Patent
Shintou et al.

(10) Patent No.: US 9,691,517 B2
(45) Date of Patent: Jun. 27, 2017

(54) HYDROXY COMPOUND, ION CONDUCTING AGENT, AND ELECTROCONDUCTIVE RESIN COMPOSITION

(71) Applicant: CANON KABUSHIKI KAISHA, Tokyo (JP)

(72) Inventors: Taichi Shintou, Saitama (JP); Masaki Yamada, Mishima (JP); Sosuke Yamaguchi, Susono (JP); Kazuhiro Yamauchi, Suntou-gun (JP); Takeshi Miyazaki, Ebina (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 136 days.

(21) Appl. No.: 14/701,837

(22) Filed: May 1, 2015

(65) Prior Publication Data

US 2015/0332803 A1 Nov. 19, 2015

(30) Foreign Application Priority Data

May 15, 2014 (JP) .................................. 2014-101639
Apr. 9, 2015 (JP) .................................. 2015-080045

(51) Int. Cl.
*H01B 1/12* (2006.01)
*C08G 18/32* (2006.01)
(Continued)

(52) U.S. Cl.
CPC ........... *H01B 1/122* (2013.01); *C07C 215/10* (2013.01); *C07C 215/12* (2013.01);
(Continued)

(58) Field of Classification Search
CPC .......... H01B 1/12; H01B 1/121; H01B 1/122; H01B 1/124; H01B 1/125; H01B 1/20;
(Continued)

(56) References Cited

U.S. PATENT DOCUMENTS 6,992,045 B2 * 1/2006 Xu .................. A01N 37/04
504/206
7,347,954 B2 * 3/2008 Banno ................ C07C 219/08
252/62.2
(Continued)

FOREIGN PATENT DOCUMENTS

JP 2009-144051 A 7/2009

OTHER PUBLICATIONS

Shintou et al., U.S. Appl. No. 14/708,515, filed May 11, 2015.
(Continued)

*Primary Examiner* — Harold Pyon
*Assistant Examiner* — Matthew R Diaz
(74) *Attorney, Agent, or Firm* — Fitzpatrick, Cella, Harper & Scinto

(57) ABSTRACT

Provided are a hydroxy compound and an ion conducting agent each having excellent electroconductivity. Also provided is an electroconductive resin composition suppressed in bleeding and excellent in electroconductivity through the use of the hydroxy compound. Specifically, provided are a hydroxy compound represented by the following general formula (1), and an ion conducting agent including the hydroxy compound.

General formula (1)

Cation species (Continued)

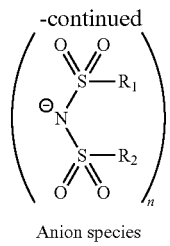

Anion species

6 Claims, 1 Drawing Sheet

(51) Int. Cl.
| | |
|---|---|
| C07C 215/10 | (2006.01) |
| C07C 215/12 | (2006.01) |
| C07C 215/14 | (2006.01) |
| C07C 215/18 | (2006.01) |
| C07C 311/09 | (2006.01) |
| C07C 311/32 | (2006.01) |
| C08G 18/48 | (2006.01) |
| C08G 18/08 | (2006.01) |
| C07C 215/40 | (2006.01) |
| C07D 213/04 | (2006.01) |
| C07D 207/06 | (2006.01) |
| C07C 217/08 | (2006.01) |
| C07D 285/15 | (2006.01) |
| C07D 233/61 | (2006.01) |
| C07C 311/48 | (2006.01) |
| C08G 18/38 | (2006.01) |
| C08G 18/76 | (2006.01) |

(52) U.S. Cl.
CPC .......... *C07C 215/14* (2013.01); *C07C 215/18* (2013.01); *C07C 215/40* (2013.01); *C07C 217/08* (2013.01); *C07C 311/09* (2013.01); *C07C 311/32* (2013.01); *C07C 311/48* (2013.01); *C07D 207/06* (2013.01); *C07D 213/04* (2013.01); *C07D 233/61* (2013.01); *C07D 285/15* (2013.01); *C08G 18/0814* (2013.01); *C08G 18/3275* (2013.01); *C08G 18/3278* (2013.01); *C08G 18/3281* (2013.01); *C08G 18/3284* (2013.01); *C08G 18/3861* (2013.01); *C08G 18/48* (2013.01); *C08G 18/7671* (2013.01); *H01B 1/125* (2013.01)

(58) Field of Classification Search
CPC .. C07D 207/06; C07D 213/04; C07D 285/15; C01G 18/48; C01G 18/5015; C01G 18/5021; C01G 18/5024; C07C 215/02; C07C 215/10; C07C 215/18; C07C 215/40; C07C 217/02; C07C 217/08; C07C 311/00; C07C 311/09; C07C 311/10; C07C 311/31; C07C 311/32; C07C 311/48; C08G 18/0814; C08G 18/3275; C08G 18/3278; C08G 18/3281; C08G 18/3284; C08G 18/3861
See application file for complete search history.

(56) References Cited

U.S. PATENT DOCUMENTS

| | | | |
|---|---|---|---|
| 2007/0185330 A1* | 8/2007 | Walker | B01J 31/003 546/184 |
| 2008/0221361 A1* | 9/2008 | Walker | B01J 31/003 564/508 |
| 2009/0045373 A1* | 2/2009 | Hammami | C01B 21/086 252/62.2 |
| 2011/0045359 A1* | 2/2011 | Schmidt | C07C 211/63 429/338 |
| 2013/0156992 A1 | 6/2013 | Okumura et al. | |
| 2013/0323155 A1* | 12/2013 | Tsubokura | C07C 303/40 423/386 |
| 2015/0329474 A1 | 11/2015 | Shintou et al. | |

OTHER PUBLICATIONS

Takuya Iwata et al., "Fixation of Ionic Liquids Into Polyether-Based Polyurethane Films to Maintain Long-Term Antistatic Properties," 55 Polymer 2501-2504 (Mar. 2014).
Examination Report in German Application No. 10 2015 107 510.5 (Jun. 7, 2016).
First Office Action in Chinese Application No. 201510246116.8 (Nov. 3, 2016).

* cited by examiner

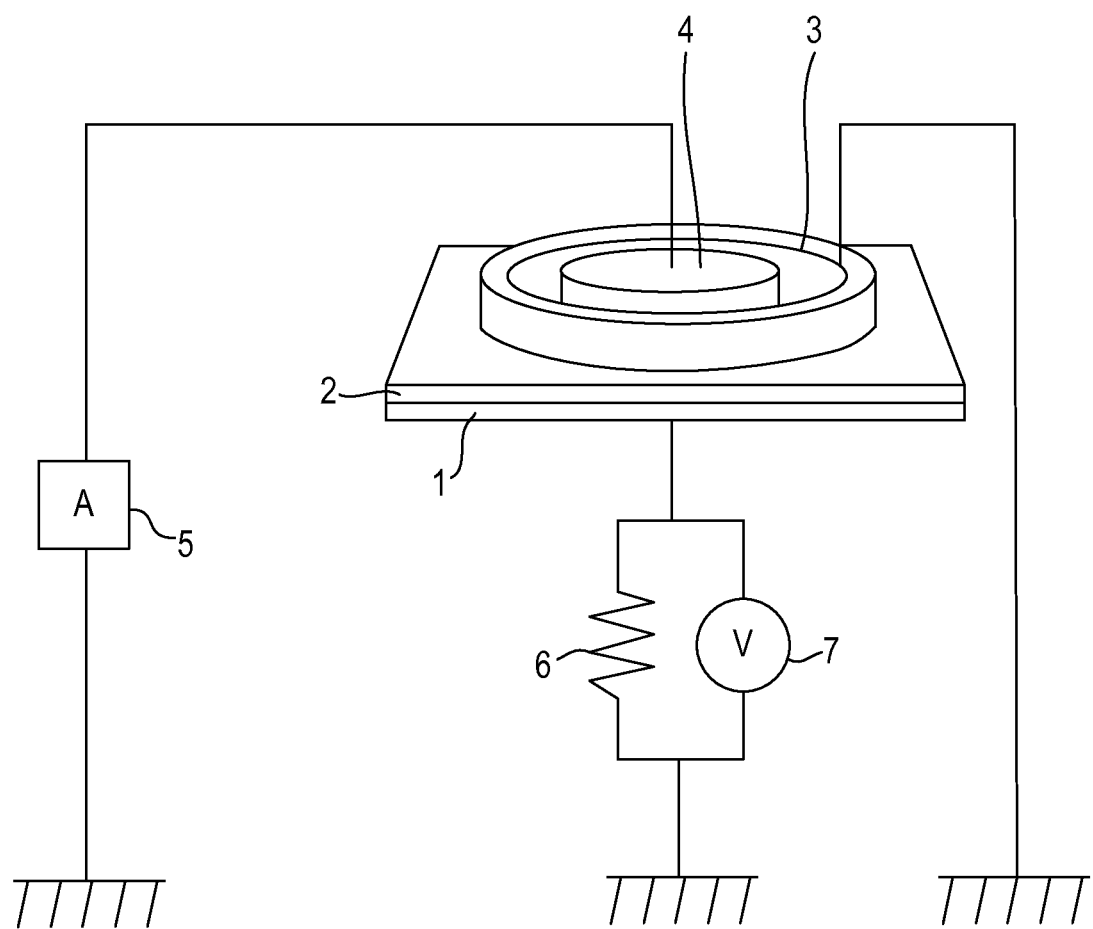

HYDROXY COMPOUND, ION CONDUCTING AGENT, AND ELECTROCONDUCTIVE RESIN COMPOSITION

BACKGROUND OF THE INVENTION

Field of the Invention

The present invention relates to a hydroxy compound, an ion conducting agent, and an electroconductive resin composition.

Description of the Related Art

In recent years, a synthetic resin has been utilized in various fields such as precision instruments such as a liquid crystal display and an optical lens, automobile parts, substrates for magnetic recording media such as an optical disk, and protective films for semiconductor materials and the like. The synthetic resin is lightweight and excellent in toughness as compared with a glass product. On the other hand, the resin is liable to be charged and dust is liable to adhere to the resin. Accordingly, a technology involving adding an ion conducting agent to an insulating resin to make the resin electroconductive has been known.

In addition, Japanese Patent Application Laid-Open No. 2009-144051 (Patent Literature 1) discloses an ion conducting agent intended for the following purpose. The agent is added to an insulating resin to impart electroconductivity to the resin, thereby providing an electroconductive resin. The incorporation of the ion conducting agent disclosed in Patent Literature 1 improves the electroconductivity of the electroconductive resin. Moreover, even when an environment where the resin is used changes, the extent to which the electroconductivity changes with time is small and the occurrence of the bleeding of the agent is suppressed. However, according to investigations made by the inventors of the present invention, the ion conducting agent according to Patent Literature 1 has not reached performance required by the inventors of the present invention yet.

SUMMARY OF THE INVENTION

In view of the foregoing, one embodiment of the present invention is directed to providing a hydroxy compound and an ion conducting agent each having an excellent ability to impart electroconductivity to an insulating resin. Another embodiment of the present invention is directed to providing an ion conducting agent capable of imparting high electroconductivity. In addition, another embodiment of the present invention is directed to providing an electroconductive resin composition stably showing high electroconductivity.

According to one aspect of the present invention, there is provided a hydroxy compound represented by the following general formula (1).

General formula (1)

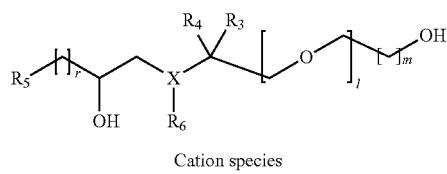

Cation species

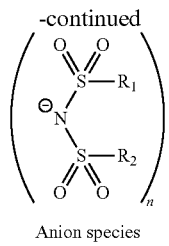

Anion species

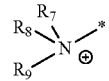

General formula (2)

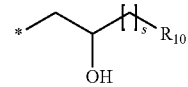

General formula (3)

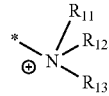

General formula (4)

In the general formula (1), $R_1$ and $R_2$ each independently represent a fluorine atom, or a linear or branched fluoroalkyl group having 1 or more and 8 or less carbon atoms, or $R_1$ and $R_2$ are bonded to each other to represent an atomic group needed for forming a ring structure containing a fluorine atom together with two sulfur atoms and one nitrogen atom. $R_3$ and $R_4$ each independently represent a hydrogen atom, or a substituted or unsubstituted alkyl group having 1 or more and 20 or less carbon atoms, $R_5$ represents a hydroxyl group, an amino group, or a group represented by the general formula (2), $R_6$ represents a substituted or unsubstituted alkyl group having 1 or more and 4 or less carbon atoms, or a group represented by the general formula (3), X represents a nitrogen atom or $-N^+(-R_{14})-$, and $R_{14}$ represents a substituted or unsubstituted alkyl group having 1 or more and 4 or less carbon atoms, or $R_6$ and $R_{14}$ are bonded to each other to represent an atomic group needed for forming a nitrogen-containing heterocycle. In the general formula (2), $R_7$, $R_8$, and $R_9$ each independently represent a substituted or unsubstituted alkyl group having 1 or more and 20 or less carbon atoms, or any two groups selected from $R_7$ to $R_9$ are bonded to each other to represent an atomic group needed for forming a ring structure together with one nitrogen atom. In the general formula (3), $R_{10}$ represents a hydroxyl group, an amino group, or a group represented by the general formula (4). In the general formula (4), $R_{11}$, $R_{12}$, and $R_{13}$ each independently represent a substituted or unsubstituted alkyl group having 1 or more and 20 or less carbon atoms, or any two groups selected from $R_{11}$, $R_{12}$, and $R_{13}$ are bonded to each other to represent an atomic group needed for forming a ring structure together with one nitrogen atom. l represents an integer of from 1 to 20. When l represents 0, m represents an integer of from 1 to 20, and when l represents an integer of from 1 to 20, m represents 1. n represents an integer of from 1 to 2, r and s each independently represent an integer of from 1 to 20, and the symbol "*" represents a bonding site.

In addition, according to another aspect of the present invention, there is provided an ion conducting agent containing the hydroxy compound.

Further, according to still another aspect of the present invention, there is provided an electroconductive resin composition obtained by causing the hydroxy compound and a polyisocyanate compound to react with each other.

According to the embodiments of the present invention, the hydroxy compound and the ion conducting agent each having excellent electroconductivity can be provided. In addition, when the hydroxy compound and a resin are caused to react with each other, the hydroxy compound is fixed to the resin. Accordingly, the electroconductive resin composition suppressed in bleeding and excellent in electroconductivity can be provided.

Further features of the present invention will become apparent from the following description of exemplary embodiments with reference to the attached drawing.

BRIEF DESCRIPTION OF THE DRAWINGS

FIGURE is a view for illustrating the outline of A machine for measuring the current value of an electroconductive resin composition according to the present invention.

DESCRIPTION OF THE EMBODIMENTS

Hereinafter, the present invention is described in more detail.

The inventors of the present invention have made extensive investigations in order to obtain an ion conducting agent that can impart additionally excellent electroconductivity to an insulating resin.

As a result, the inventors have found that a hydroxy compound having cation species and anion species, represented by the following general formula (1) is extremely excellent in electroconductivity. In addition, the inventors have found that the hydroxy compound serves as, for example, an excellent ion conducting agent that can provide a resin composition having high electroconductivity when mixed with an insulating resin.

Further, the inventors have found that causing the hydroxy compound to react with, for example, a polyisocyanate compound provides an electroconductive resin having fixed thereto an ion exchange group, the resin being suppressed in bleeding additionally well and excellent in electroconductivity.

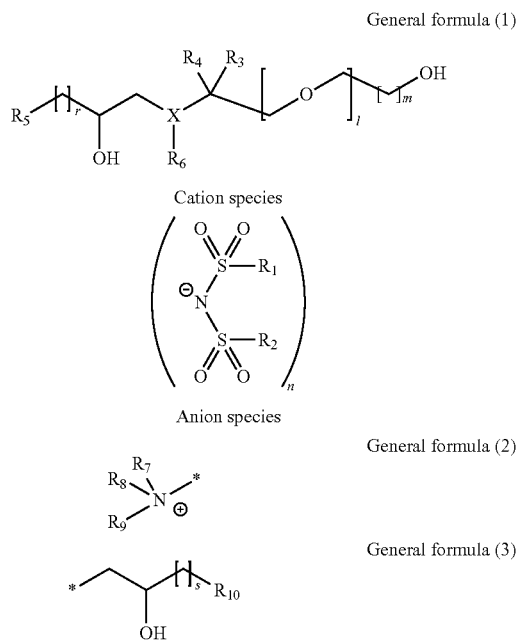

General formula (1)

Cation species

Anion species

General formula (2)

General formula (3)

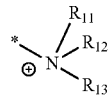

General formula (4)

In the general formula (1), $R_1$ and $R_2$ each independently represent a fluorine atom, or a linear or branched fluoroalkyl group having 1 or more and 8 or less carbon atoms, or $R_1$ and $R_2$ are bonded to each other to represent an atomic group needed for forming a ring structure containing a fluorine atom together with two sulfur atoms and one nitrogen atom. Herein, it is preferred that the linear or branched fluoroalkyl group having 1 or more and 8 or less carbon atoms that may be represented by $R_1$ or $R_2$ be preferably a perfluoroalkyl.

$R_3$ and $R_4$ each independently represent a hydrogen atom, or a substituted or unsubstituted linear or branched alkyl group having 1 or more and 20 or less carbon atoms. The alkyl group that may be represented by $R_3$ or $R_4$ may be substituted by a halogen atom such as a chlorine atom, a fluorine atom, or a bromine atom or a hydroxyl group.

$R_5$ represents a hydroxyl group, an amino group, or a group represented by the general formula (2).

$R_6$ represents a substituted or unsubstituted alkyl group having 1 or more and 4 or less carbon atoms, or a group represented by the general formula (3), or represents an atomic group needed for forming a nitrogen-containing heterocycle by being bonded to $R_{14}$ to be described later.

X represents a nitrogen atom or —$N^+$(—$R_{14}$)—, and $R_{14}$ represents a substituted or unsubstituted alkyl group having 1 or more and 4 or less carbon atoms, or $R_6$ and $R_{14}$ are bonded to each other to represent an atomic group needed for forming a nitrogen-containing heterocycle described above.

In the general formula (2), $R_7$, $R_8$, and $R_9$ each independently represent a substituted or unsubstituted alkyl group having 1 or more and 20 or less carbon atoms, or any two groups selected from $R_7$ to $R_9$ are bonded to each other to represent an atomic group needed for forming a nitrogen-containing heterocycle.

In the general formula (3), $R_{10}$ represents a hydroxyl group, an amino group, or a group represented by the general formula (4).

In the general formula (4), $R_{11}$, $R_{12}$, and $R_{13}$ each independently represent a substituted or unsubstituted alkyl group having 1 or more and 20 or less carbon atoms, or any two groups selected from $R_{11}$, $R_{12}$, and $R_{13}$ are bonded to each other to represent an atomic group needed for forming a nitrogen-containing heterocycle.

l represents an integer of from 0 to 20. When l represents 0, m represents an integer of from 1 to 20. In addition, when l represents an integer of from 1 to 20, m represents 1.

n represents an integer of from 1 to 2.

r and s each independently represent an, integer of from 1 to 20.

Further, the symbol "*" represents a bonding site.

First, the hydroxy compound, which has cation species and anion species, represented by the general formula (1) is described.

In the general formula (1), the fluoroalkyl group that may be represented by $R_1$ or $R_2$ is a fluoroalkyl group having 1 or more and 8 or less carbon atoms. A preferred example thereof is a linear or branched perfluoroalkyl group having 1 or more and 8 or less carbon atoms. Specific examples thereof include a trifluoromethyl group, a perfluoroethyl group, a perfluoropropyl group, a perfluorobutyl group, and a perfluorooctyl group. Of those, a trifluoromethyl group or a perfluoroethyl group is preferred because of imparting high electroconductivity to the hydroxy compound. It should be noted that the perfluoroalkyl group of the present invention refers to an alkyl group in which all hydrogen atoms bonded to a carbon atom in the alkyl group are substituted by fluorine atoms.

In the general formula (1), the ring structure containing a fluorine atom formed by bonding $R_1$ and $R_2$ to each other together with two sulfur atoms and one nitrogen atom is not particularly limited, and an example thereof is the following structure.

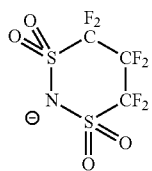

In the general formula (1), the alkyl group represented by $R_3$ or $R_4$ is not particularly limited. Examples thereof include saturated or unsaturated, linear, branched, or cyclic primary to tertiary alkyl groups each having 1 to 20 carbon atoms such as a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group, and a cyclohexenylethyl group. In particular, a methyl group, an ethyl group, or a n-propyl group is preferred because of excellence in electroconductivity.

It is particularly preferred that $R_3$ and $R_4$ each represent a hydrogen atom because of excellence in electroconductivity.

As described above, in the general formula (1), $R_3$ and $R_4$ may each represent an alkyl group having a hydroxyl group, i.e., a hydroxyalkyl group. The hydroxyalkyl group represented by $R_3$ or $R_4$ is not particularly limited. Examples thereof include a hydroxyethyl group, a hydroxypropyl group, and a hydroxybutyl group.

In the general formula (1), the amino group represented by $R_5$ is not particularly limited. Examples thereof include a methylamino group, an ethylamino group, a dimethylamino group, a diethylamino group, a piperidyl group, and a pyrrolidyl group.

In the general formula (1), the alkyl group represented by $R_6$ is not particularly limited as long as it is an alkyl group having 1 or more and 4 or less carbon atoms. Examples thereof include a methyl group, an ethyl group, a propyl group, and a butyl group. Of those, a methyl group or an ethyl group is preferred.

In the general formula (1), the alkyl group represented by $R_{14}$ in the case where X represents —$N^+$(—$R_{14}$)— is not particularly limited as long as it is an alkyl group having 1 or more and 4 or less carbon atoms. Examples thereof include a methyl group, an ethyl group, a propyl group, and a butyl group. Of those, a methyl group or an ethyl group is preferred.

In the general formula (1), the ring (nitrogen-containing heterocycle) formed by bonding $R_6$ and $R_{14}$ to each other is not particularly limited. Examples thereof include a pyrrolidine ring, a pyridine ring, an indazoline ring, a 1,4-diazabicyclo[2.2.2]octane ring, and a piperidine ring.

In the general formula (2), the alkyl group represented by any one of $R_7$, $R_8$, and $R_9$ is not particularly limited as long as it is a linear, branched, or cyclic alkyl group having 1 or more and 20 or less carbon atoms. Specific examples thereof include a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group, and a cyclohexenylethyl group. In particular, it is preferred that the alkyl group be an alkyl group having 1 to 4 carbon atoms such as a methyl group, an ethyl group, a n-propyl group, an iso-propyl group, or a n-butyl group. It is particularly preferred that the alkyl group be a methyl group because of excellence in electroconductivity.

In the general formula (2), the ring structure formed by bonding any two groups selected from $R_7$, $R_8$, and $R_9$ together with one nitrogen atom is not particularly limited. Examples thereof include a pyrrolidine ring, a pyridine ring, an indazoline ring, a 1,4-diazabicyclo[2.2.2]octane ring, and a piperidine ring.

In the general formula (3), the amino group represented by $R_{10}$ is not particularly limited. Examples thereof include a methylamino group, an ethylamino group, a dimethylamino group, a diethylamino group, a piperidyl group, and a pyrrolidyl group.

In the general formula (4), the alkyl group represented by any one of $R_{11}$, $R_{12}$, and $R_{13}$ is not particularly limited as long as it is a linear, branched, or cyclic alkyl group having 1 or more and 20 or less carbon atoms. Specific examples thereof include a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group, and a cyclohexenylethyl group. Of those, from the viewpoint of increasing the electroconductivity of the hydroxy compound according to the present invention, an alkyl group having 1 to 4 carbon atoms (such as a methyl group, an ethyl group, a n-propyl group, an iso-propyl group, or a n-butyl group) is preferred and a methyl group is particularly preferred.

In the general formula (4), the ring structure formed by bonding any two groups selected from $R_{11}$, $R_{12}$, and $R_{13}$ together with one nitrogen atom is not particularly limited. Examples thereof include a pyrrolidine ring, a pyridine ring, an indazoline ring, a 1,4-diazabicyclo[2.2.2]octane ring, and a piperidine ring.

The alphabet l (lower-case l) represents an integer of from 0 to 20. When l represents 0, m represents an integer of from 1 to 20, and when l represents an integer of from 1 to 20, m represents 1. The case where l represents 0 is particularly preferred because good electroconductivity is obtained.

It should be noted that when X in the hydroxy compound represented by the general formula (1) according to the present invention represents a nitrogen atom, one, or each of both, of $R_5$ and $R_6$ satisfies the following condition (i) or (ii):
(i) $R_5$ represents a group represented by the general formula (2); and
(ii) $R_6$ represents a group represented by the general formula (3), and $R_{10}$ in the general formula (3) represents a group represented by the general formula (4).

The hydroxy compound having a structure represented by the general formula (1) according to the present invention can be synthesized with reference to a known method based on a combination of, for example, the synthesis of a halogenated quaternary ammonium salt by the nucleophilic reaction of a tertiary amine with respect to an alkyl halide, and an anion exchange reaction between the halogenated quaternary ammonium salt and an alkali metal salt of a fluorine-based anion compound.

Modes A to C for a method of producing the hydroxy compound having a structure represented by the general formula (1) of the present invention are described below, but the production method is not limited thereto.

<Mode A: When Secondary Amine is used as Amine Compound>

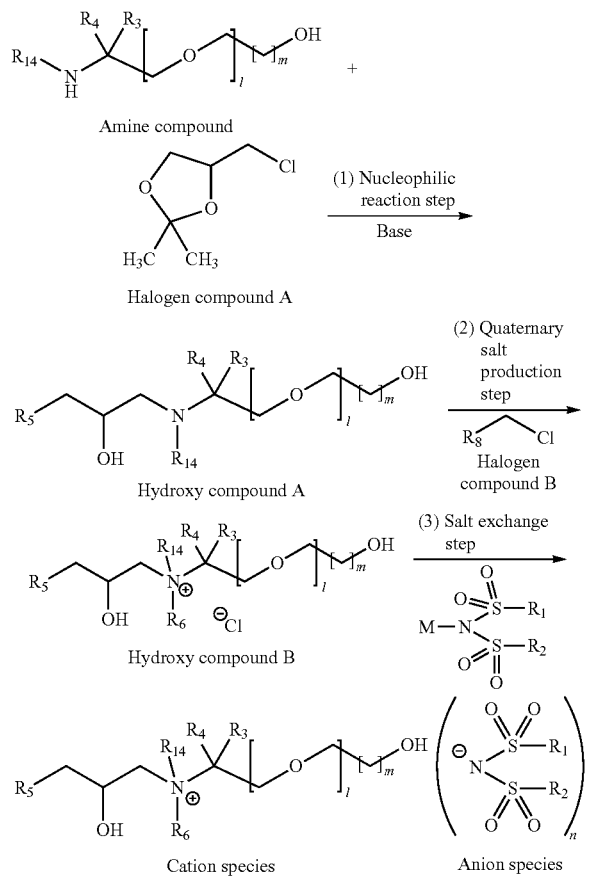

It should be noted that $R_1$ to $R_6$, $R_{14}$, l, m, and n in the respective compounds in the reaction formulae and the compound having a structure represented by the general formula (1) each have the same meaning as that described in the foregoing. In addition, M represents an alkali metal such as Li, K, Na, or Cs.

That is, the hydroxy compound represented by the general formula (1) of the present invention can be obtained through (1) the nucleophilic reaction step, (2) the quaternary salt production step, and (3) the salt exchange step.

<Re: (1) Nucleophilic Reaction Step>

First, (1) the nucleophilic reaction step of obtaining the hydroxy compound A is described.

The nucleophilic reaction step is the step of causing the amine compound and the halogen compound A to react with each other to provide the hydroxy compound A.

The nucleophilic reaction step is preferably performed in the presence of a solvent, though the reaction can be performed in the absence of any solvent. The solvent is not particularly limited as long as the solvent is not involved in the reaction, and examples thereof include acetonitrile, heptane, toluene, and N,N-dimethylformamide (hereinafter abbreviated as "DMF"). In addition, two or more kinds of solvents can be used as a mixture, and a mixing ratio upon use of the solvents as a mixture can be arbitrarily determined. Of those, acetonitrile is particularly preferred.

The reaction solvent is used in an amount in the range of preferably from 0.1 mass % to 1,000 mass %, more preferably from 1.0 mass % to 150 mass % with respect to the amine compound.

In addition, a base is preferably used in the nucleophilic reaction step for rapidly advancing the reaction. The base that can be used is not particularly limited as long as the base is not involved in the reaction, and examples thereof include inorganic bases such as sodium carbonate, sodium hydrogen carbonate, barium carbonate, calcium carbonate, and potassium carbonate. The base is used in an amount in the range of preferably from 0.01 mass % to 100 mass %, more preferably from 0.1 mass % to 20 mass %, still more preferably from 0.5 mass % to 5 mass % with respect to the amine compound. After the completion of the reaction, the desired hydroxy compound A can be obtained, by performing purification such as recrystallization or silica gel chromatography.

The nucleophilic reaction step is performed at a reaction temperature in the range of preferably from −20° C. to 250° C., more preferably from 0° C. to 150° C. The reaction is typically completed within 48 hours.

<Re: (2) Quaternary Salt Production Step>

Next, (2) the quaternary salt production step of obtaining the hydroxy compound B is described.

The quaternary salt production step is the step of causing the hydroxy compound A and the halogen compound. B to react with each other to provide a quaternary salt (hydroxy compound B).

The quaternary salt production step is preferably performed in the presence of a solvent, though the reaction can be performed in the absence of any solvent. The solvent is not particularly limited as long as the solvent is not involved in the reaction, and examples thereof include acetonitrile, heptane, toluene, and N,N-dimethylformamide (hereinafter abbreviated as "DMF"). In addition, two or more kinds of solvents can be used as a mixture, and a mixing ratio upon use of the solvents as a mixture can be arbitrarily determined. Of those, acetonitrile is particularly preferred.

The quaternary salt production step is performed at a reaction temperature in the range of preferably from −20° C. to 250° C., more preferably from −0° C. to 150° C. The reaction is typically completed within 48 hours. When the boiling point of the tertiary amine is low, the reaction is performed by using a pressure-resistant closed vessel.

After the completion of the reaction, the desired quaternary salt can be obtained by performing purification such as recrystallization or silica gel chromatography, <Re: (3) Salt Exchange Step>

Next, (3) the salt exchange step of obtaining one mode of the general formula (1) is described.

The step is the step of obtaining the hydroxy compound having a structure represented by the general formula (1) through an anion exchange reaction between the quaternary salt and an alkali metal salt of a fluorine-based anion compound.

A solvent in the salt exchange step is, for example, a polar solvent such as water, an alcohol, acetone, or acetonitrile, or a nonpolar solvent such as hexane or heptane. The solvent can be selected in consideration of the properties of an ion conducting agent to be produced. For example, when the ion conducting agent to be produced is water-insoluble, the reaction is preferably performed in water by using water as the solvent. Further, a halogenated metal salt to be produced as a by-product can be easily removed by washing the resultant reaction liquid with water. On the other hand, when the ion conducting agent to be produced is water-soluble, a halogenated metal salt to be produced as a by-product can be easily removed by selecting and using a solvent in which the halogenated metal salt does not dissolve.

The alkali, metal salt of the fluorine-based anion compound that can be used in the salt exchange step is not particularly limited, but suitable examples thereof can include the following anion compounds (1) to (8).

Anion compound (1)

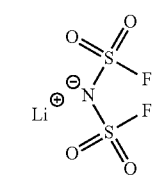

Anion compound (2)

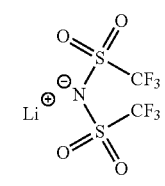

Anion compound (3)

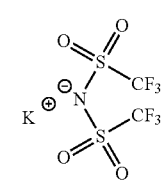

Anion compound (4)

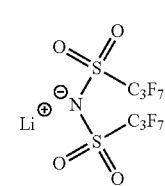

Anion compound (5)

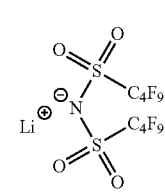

Anion compound (6)

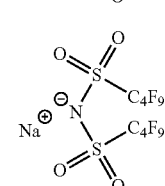

Anion compound (7)

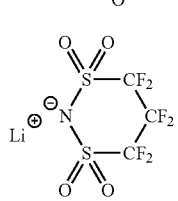

Anion compound (8)

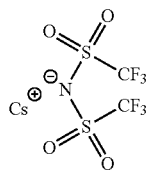

Of those, the anion compound (1), (2), (3), (5), or (7) is particularly preferred because of its ease of handling and excellent electroconductivity.

In addition, a halogen ion scavenger can be used in the salt exchange step. The halogen ion scavenger is not particularly limited, but examples thereof include silver nitrate and an ion exchange resin.

After the completion of the reaction, the hydroxy compound having a structure represented by the general formula (1) can be obtained by performing purification such as silica gel chromatography.

<Mode B: When Tertiary Amine is used as Amine Compound>

When a tertiary amine is used as the amine compound instead of the use of the secondary amine in the mode A, (1) the nucleophilic reaction step in the mode A can be omitted. That is, when the tertiary amine is used, the hydroxy compound represented by the general formula (1) of the present invention can be obtained through (5) a quaternary salt production step and (6) a salt exchange step. (2) The quaternary salt production step in the mode A and (5) the quaternary salt production step in the mode B are identical in meaning to each other, and (3) the salt exchange step in the mode A and (6) the salt exchange step in the mode B are also identical in meaning to each other.

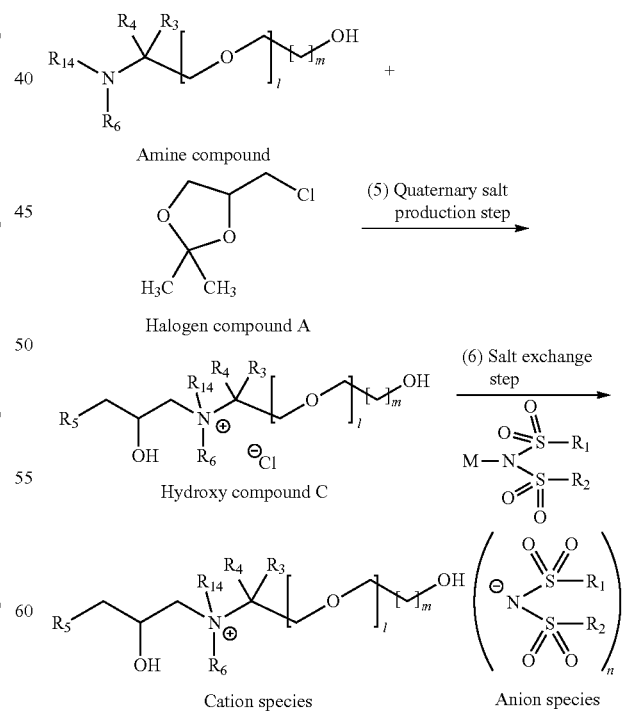

It should be noted that $R_1$ to $R_6$, $R_{14}$, l, m, and n in the respective compounds in the reaction formulae and the compound having a structure represented by the general formula (1) each have the same meaning as that described in the foregoing. In addition, M represents an alkali metal such as Li, K, Na, or Cs.

<Mode C: When 2-(Chloromethyl) oxirane is used as Halogen Compound>

When 2-(chloromethyl) oxirane is used as a halogen compound, the hydroxy compound represented by the general formula (1) of the present invention can be obtained through (7) a nucleophilic reaction step, (8) a quaternary salt production step, and (9) a salt exchange step.

(1) The nucleophilic reaction step in the mode A and (7) the nucleophilic reaction step in the mode C are identical in meaning to each other, the quaternary salt production step in the mode A and (8) the quaternary salt production step in the mode C are also identical in meaning to each other, and (3) the salt exchange step in the mode A and (9) the salt exchange step in the mode C are also identical in meaning to each other.

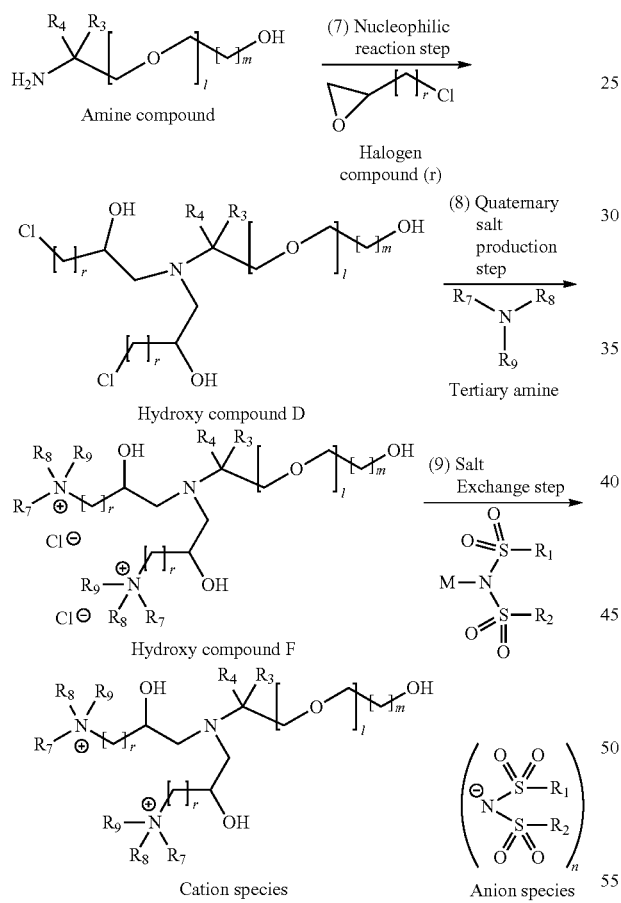

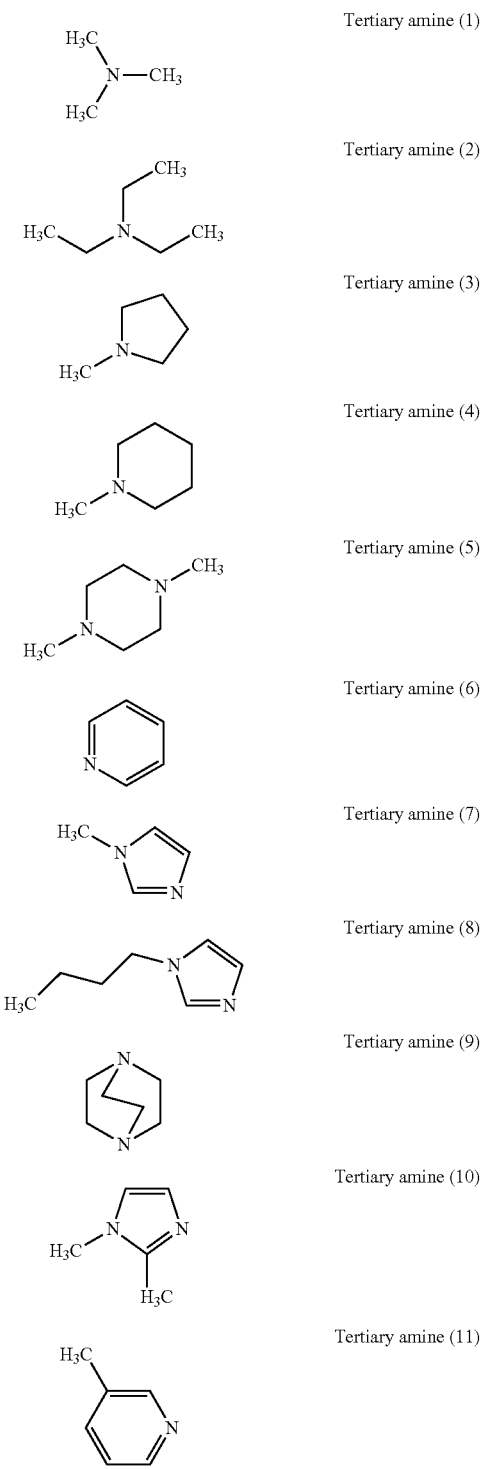

It should be noted that $R_1$ to $R_{13}$, l, m, n, and r in the respective compounds in the reaction formulae and the compound having a structure represented by the general formula (1) each have the same meaning as that described in the foregoing. In addition, M represents an alkali metal such as Li, K, Na, or Cs.

The tertiary amine that can be used in the quaternary salt production step is not particularly limited, but suitable examples thereof can include the following tertiary amines (1) to (11).

Of those, the tertiary amine (1), (2), (7), or (10) is particularly preferred because of its excellent electroconductivity.

Compounds (1) to (21) are shown below as preferred examples of the hydroxy compound of the present invention, but the compound is not limited to the following compounds.

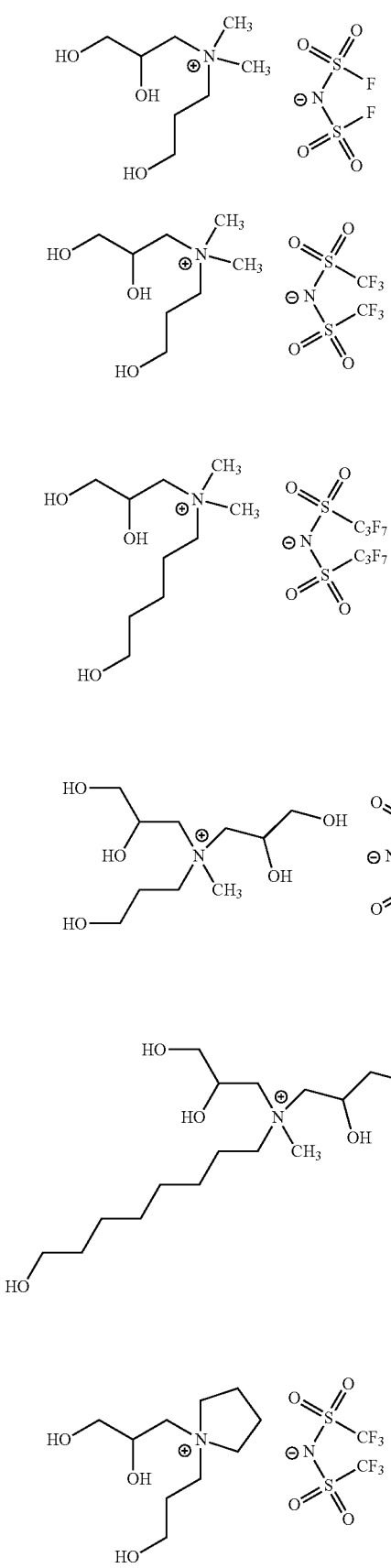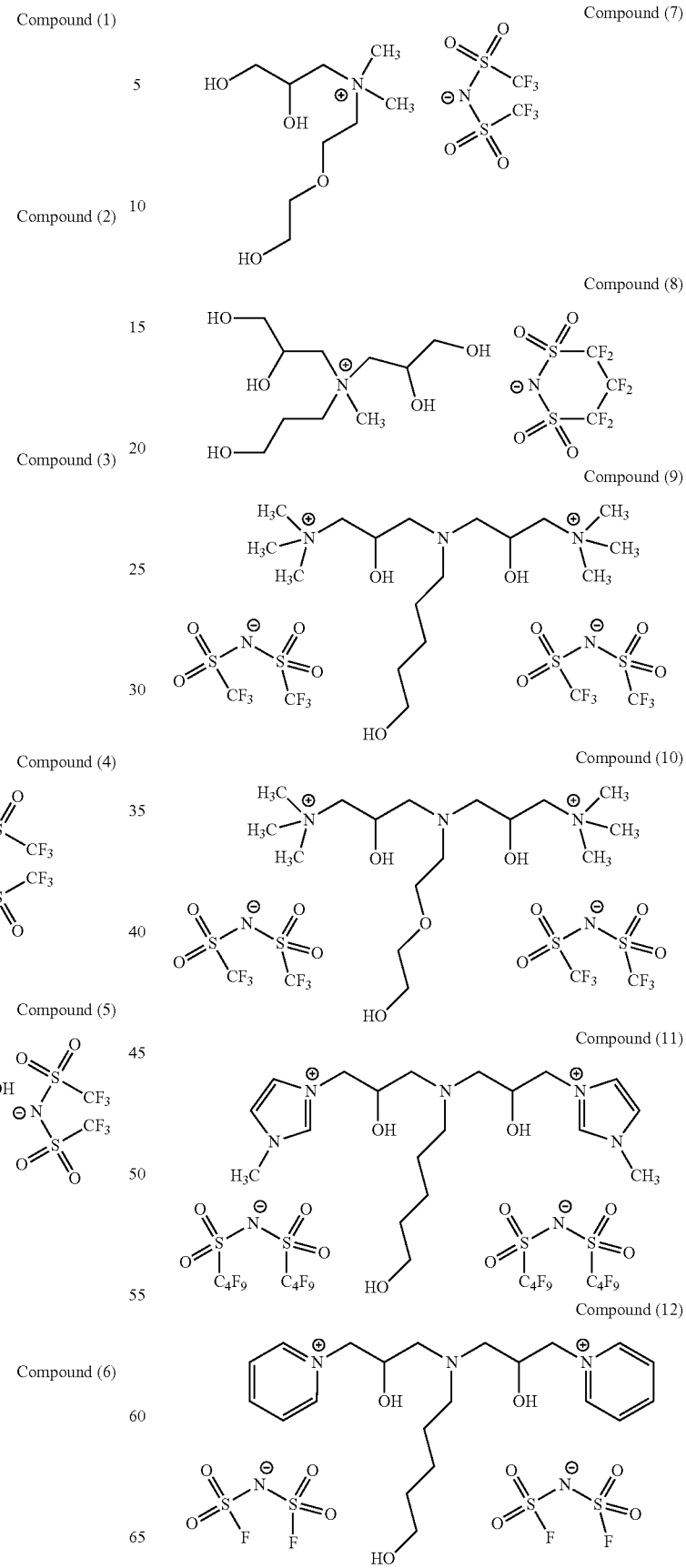

-continued

Compound (13)
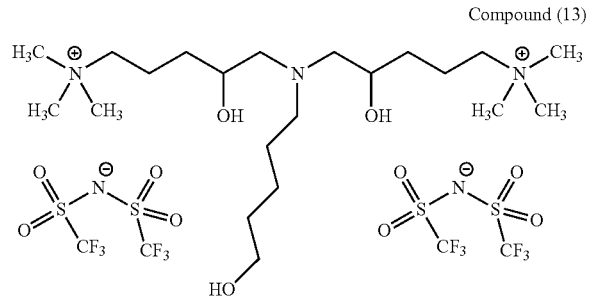

Compound (14)
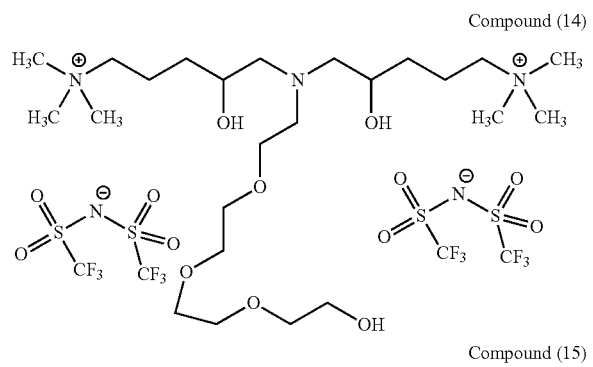

Compound (15)
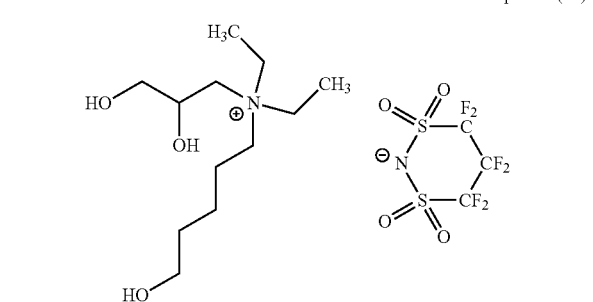

Compound (16)
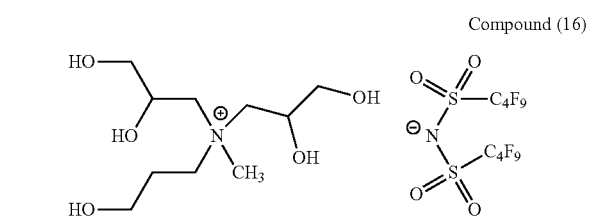

Compound (17)
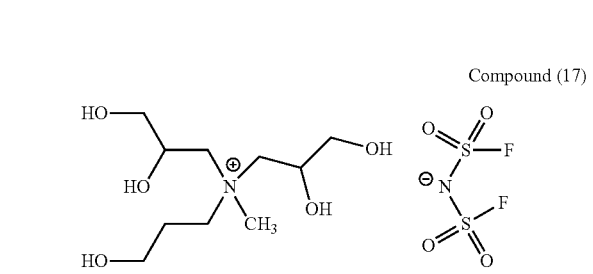

Compound (18)
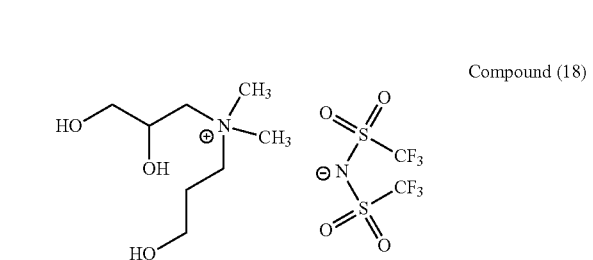

Compound (19)
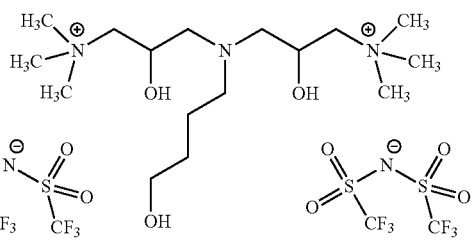

Compound (20)
Compound (21)
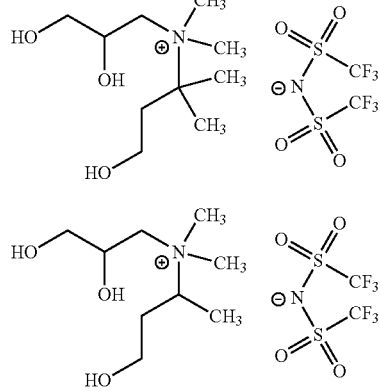

The hydroxy compound according to the present invention can be suitably used as an ion conducting agent because the compound has the following property: the compound serves as a molten salt formed of a cation and an anion at least at a certain temperature in the range of from 0° C. to 300° C.

<Re: Electroconductive Resin Composition>

The hydroxy compound according to the present invention can impart high electroconductivity to a resin. That is, the use of the hydroxy compound according to the present invention provides an electroconductive resin composition excellent in electroconductivity.

First, an electroconductive resin composition according to the present invention is described.

The electroconductive resin composition according to the present invention can be obtained by kneading the hydroxy compound having a structure represented by the general formula (1) of the present invention and a general resin such as a thermoplastic resin, a UV-curable resin, a rubber, or a pressure-sensitive adhesive. The general-purpose resin such as a thermoplastic resin, a UV-curable resin, a rubber, or a pressure-sensitive adhesive as used herein may contain a polyisocyanate group (polyisocyanate compound) or may not contain such group.

The thermoplastic resin to be used in the present invention is not particularly limited. Examples thereof include a polyolefin-based resin, a polyacrylic resin, a polystyrene resin, a polyester resin, a polyurethane resin, a polycarbonate resin, a polyvinyl chloride resin, and an epoxy resin.

The UV-curable resin to be used in the present invention is not particularly limited. An example thereof is diethylene glycol di(meth)acrylate.

The rubber to be used in the present invention is not particularly limited. Examples thereof include acrylic rubber, urethane rubber, styrene-butadiene copolymer rubber, epichlorohydrin-ethylene oxide copolymer rubber, epichlorohydrin-ethylene oxide-allyl glycidyl ether copolymer rubber, acrylonitrile-butadiene rubber, epichlorohydrin rubber, and silicone rubber.

The pressure-sensitive adhesive to be used in the present invention is not particularly limited. Examples thereof include an acrylic pressure-sensitive adhesive, a rubber-based pressure-sensitive adhesive, and a silicone-based pressure-sensitive adhesive.

In addition, the electroconductive resin composition of the present invention can be provided as a urethane resin by mixing the hydroxy compound having a structure represented by the general formula (1) and an isocyanate group-containing substance (polyisocyanate), and causing the mixture to react with a polyol compound. The urethane resin thus obtained has the following characteristic: the hydroxy compound according to the present invention reacts with an isocyanate group and is hence fixed in the urethane resin. Accordingly, such bleeding that the hydroxy compound in the ion conducting agent present in the resin migrates to the surface of the resin with the lapse of time can be suppressed, and hence the resin is excellent in temporal stability of its electroconductivity and storage stability.

The polyisocyanate to be used in the present invention is not particularly limited as long as the polyisocyanate contains two or more isocyanate groups. Specific examples thereof include 4,4'-diphenylmethane diisocyanate (MDI), isophorone diisocyanate, 4,4'-dicyclohexyl diisocyanate, trimethylhexamethylene diisocyanate, tolylene diisocyanate, a carbodiimide-modified diisocyanate, polymethylenephenyl polyisocyanate, o-toluidine diisocyanate, naphthalene diisocyanate, xylene diisocyanate, hexamethylene diisocyanate, p-phenylene diisocyanate, lysine diisocyanate methyl ester, and dimethyl diisocyanate. One kind of these polyisocyanates may be used alone, or two or more kinds thereof may be used in combination.

The polyol compound to be used in the present invention is not particularly limited as long as the polyol compound contains two or more hydroxyl groups. Specifically, polyether polyol, polyester polyol, or polycarbonate polyol may be used. Of those, a polyether polyol having an alkylene oxide structure is particularly preferred. One kind of these polyol compounds may be used alone, or two or more kinds thereof may be used in combination.

The usage of the hydroxy compound having a structure represented by the general formula (1) to be used in the production of the electroconductive resin composition according to the present invention can be appropriately changed depending on the target degree of the electroconductivity of the electroconductive resin composition.

The compounding amount of the hydroxy compound falls within the range of from 0.001 part by mass to 100 parts by mass, preferably from 0.01 part by mass to 50 parts by mass, particularly preferably from 0.1 part by mass to 10 parts by mass with respect to 100 parts by mass of the general-purpose resin such as a thermoplastic resin, a UV-curable resin, rubber, or a pressure-sensitive adhesive.

The compounding amount of the hydroxy compound falls within the range of from 0.001 part by mass to 100 parts by mass, preferably from 0.5 part by mass to 20 parts by mass, particularly preferably from 0.5 part by mass to 5 parts by mass with respect to 100 parts by mass of the general-purpose resin containing a polyisocyanate group such as a thermoplastic resin, a UV-curable resin, a rubber, or a pressure-sensitive adhesive. When the compounding amount of the hydroxy compound is 0.5 part by mass or more, an electroconductivity-imparting effect by the addition of the conducting agent can be easily obtained. When the compounding amount of the hydroxy compound is 5 parts by mass or less, a change in electrical resistance of the composition with time can be reduced.

In the electroconductive resin composition of the present invention, a compounding agent may be added to the polyisocyanate group-containing substance to the extent that an effect of the present invention is not impaired. Examples of the compounding agent can include a pigment, a dye, a surfactant, a plasticizer, a UV absorber, a filler, a softening agent, a processing aid, a tackifier, an antitack agent, a dispersant, and a foaming agent.

A molded body of, for example, a film shape, a sheet shape, or a roll shape can be obtained by kneading the electroconductive resin composition of the present invention.

As described above, the electroconductive resin composition of the present invention is formed by the reaction of the hydroxy compound of the present invention, and hence an electroconductive resin composition suppressed in bleeding and excellent in electroconductivity can be provided.

EXAMPLES

Hereinafter, the present invention is described in more detail by way of Examples and Comparative Examples. However, the present invention is not limited to Examples described below. It should be noted that, in the description, "part (s)" and "%" are by mass unless otherwise specified. The resultant compound was identified by using a $^1$H nuclear magnetic resonance spectroscopic analysis $^1$H-NMR) apparatus (ECA-400 manufactured by JEOL Ltd.) and a LC/TOF MS apparatus (LC/MSD TOF manufactured by Agilent Technologies).

[Production of Hydroxy Compound having Structure represented by General Formula (1)]

The hydroxy compound having a structure represented by the general formula (1) of the present invention can be synthesized by adding a twist to a known method.

The hydroxy compound having a structure represented by the general formula (1) of the present invention was produced by a method to be described below.

Production Example 1

Production of Compound (4)

14.8 Grams (107 mmol) of potassium carbonate was added to a solution of 15.4 mL (160 mmol) of 3-(methylamino)-1-propanol and 16.1 g (107 mmol) of 4-chloromethyl-2,2-dimethyl-1,3-dioxolane in 100 mL of acetonitrile, and the mixture was heated to reflux for 18 hours. After the completion of the reaction, the resultant was cooled to room temperature, and the precipitated solid was filtered and washed with 300 mL of acetonitrile. The filtrate was concentrated under reduced pressure, and was then purified by silica gel column chromatography to provide 5.7 g (28 mmol) of an intermediate 1.

2.1 Milliliters of α-monochlorohydrin was added to 5.0 g (24.5 mmol) of the intermediate 1, and the mixture was subjected to a reaction at 100° C. for 96 hours. After the completion of the reaction, the resultant was cooled to room temperature and diluted with 5 mL of methanol. After that, 10 mL of a 1 mol/L aqueous solution of hydrochloric acid was added to the diluted product, and the mixture was stirred at room temperature for 24 hours. After the solvent had been distilled off under reduced pressure, 24 mL of water was added to the residue, and a solution of 6.9 g (24 mmol) of lithium bistrifluoromethanesulfonylimide in 24 mL of water was dropped to the mixture. The resultant was stirred for 1 hour and then dried under reduced pressure to provide 14.1 g of the compound (4).

[Results of Analysis of Compound (4)]

[1] $^1$H-NMR (400 MHz, DMSO-d$_6$, room temperature): δ (ppm)=1.80-2.00 (2H, m), 3.14-3.36 (7H, m), 3.39-3.67 (10H, m), 4.09 (1H, br), 4.78 (4H, br).

[2] Mass spectrometry (ESI-TOF): m/z=517.8537 (M-H)$^+$.

Production Examples 2 to 4

Production of Compounds (8), (16), and (17)

The compounds (8), (16), and (17) were each obtained by performing the same synthesis as that of Example 1 except that an imide corresponding to a compound shown in Table 1 was used instead of the use of lithium bistrifluoromethanesulfonylimide in Production Example 1, and the compounds were identified by using the above-mentioned analyzers.

Production Example 5

Production of Compound (18)

10 Milliliters (75 mmol) of 4-dimethylamino-1-butanol was added to a solution of 8.3 g (75 mmol) of α-monochlorohydrin in 10 mL of water, and the mixture was stirred at 50° C. for 22 hours. After the completion of the reaction, the resultant was diluted with 60 mL of water, and a solution of 21.5 g (75 mmol) of lithium bistrifluoromethanesulfonylimide in 60 mL of water was dropped to the diluted product. The mixture was stirred for 4 hours and then concentrated under reduced pressure. 35 Milliliters of acetonitrile was added to the concentrate, and the mixture was stirred and left at rest. After that, the supernatant was decanted. The residue was dried under reduced pressure to provide 31.5 g of the compound (18).

[Results of Analysis of Compound (18)]

[1] $^1$H-NMR (400 MHz, DMSO-d$_6$, room temperature): δ (ppm)=1.39-1.46 (2H, m), 1.69-1.79 (2H, m), 3.08 (6H, d, J=1.83 Hz), 3.21-3.28 (2H, m), 4.01 (1H, br), 4.60 (1H, t, J=5.04 Hz), 5.04 (1H, t, J=5.72 Hz), 5.42 (1H, d, J=5.04 Hz).

[2] Mass spectrometry (ESI-TCF): m; z=192.1752 (cation molecule: M+H)$^+$, m/z=279.9343 (anion molecule: M+H)$^+$.

Production Example 6

Production of Compound (19)

Under a nitrogen atmosphere, 25 mL of a solution of 7 g (75 mmol) of epichlorohydrin in methanol was dropped to a solution of 2.23 g (25 mmol) of 4-amino-1-butanol in 25 ml of methanol cooled to 0° C. After the temperature of the mixture had been increased to room temperature, the mixture was stirred for 24 hours and the completion of the reaction was confirmed. The resultant was concentrated under reduced pressure, the concentrate was dissolved in 19 mL of acetonitrile, and 23 mL of a 4.3 mol/L aqueous solution of trimethylamine was added to the solution. The mixture was stirred at 100° C. for 5.5 hours in a sealed tube and cooled to room temperature, and the tube was opened while attention was paid. After the resultant had been concentrated under reduced pressure, the concentrate was suspended in 50 mL of water, and a solution of 14.6 g (50 mmol) of lithium bistrifluoromethanesulfonylimide in 50 mL of water was dropped to the suspension. After the mixture had been left to stand for 5 days, the separated oil liquid was concentrated under reduced pressure and dried to provide 16.1 g of the compound (19).

[Results of Analysis of Compound (19)]

[1] $^1$H-NMR (400 MHz, DMSO-d$_6$, room temperature): δ (ppm)=1.41 (4H, s), 2.34-2.51 (6H, m), 3.18 (18H, s), 3.34-3.42 (6H, m), 4.08 (1H, br), 4.43 (1H, t, J=4.58 Hz), 5.23 (2H, dd, J=3.89, 13.5 Hz),

[2] Mass spectrometry (EST-TOF): m/z=559.84 (cation molecule: M+H)$^+$, m/z=279.9343 (anion molecule: M+H)$^+$.

Example 1

Production of Urethane Resin Composition 1

16.6 Parts by mass of a polyisocyanate (trade name: MILLIONATE MT, MDI: manufactured by Tosoh Corporation (manufactured by former Nippon Polyurethane Industry Co., Ltd.)) and 2 parts by mass of the compound (4) were added to 83.4 parts by mass of a polyether polyol (trade name: EP505S: manufactured by Mitsui Chemicals, Inc.) so that an NCO equivalent became 1.4. It should be noted that the NCO equivalent represents a ratio ([NCO]/([OH]+[NH$_2$])) between the number of moles of an isocyanate group in the isocyanate compound and the sum of the number of moles of a hydroxyl group in the polyol component and the number of moles of an amino group of the hydroxy compound according to the present invention. Next, methyl ethyl ketone (hereinafter abbreviated as "MEK") was added to the mixture so that a total solid content ratio became 30 mass %, and the contents were mixed and stirred. The mixture was formed into a sheet shape having a thickness of 0.5 mm by a solvent casting method. Next, the sheet was subjected to a heat treatment in an oven heated to 120° C. for 3 hours. Thus, a sheet-shaped urethane resin composition 1 was produced.

Examples 2 and 3

Urethane resin compositions 2 and 3 were each produced by the same production method as that of Example 1 except that in Example 1, the compound (4) was used in a number of parts shown in Table 1 instead, of the use of 2 parts by mass of the compound, and the addition amounts of the polyether polyol and the isocyanate were adjusted so that the NCO equivalent became 1.4.

Examples 4 to 6, 8, and 9

Urethane resin compositions 4 to 8 were each produced by the same method as that of Example 1 except that in Example 1, the compound (4) was changed to a compound shown in Table 1.

Example 7

2 Parts by mass of the compound (4), 100 parts by mass of an epichlorohydrin-ethylene oxide-allyl glycidyl ether terpolymer (GECO) (trade name: EPICHLOMER CG-102, manufactured by Daiso Co., Ltd.), 5 parts by mass of zinc oxide, 35 parts by mass of calcium carbonate, 0.5 part by mass of carbon black (trade name: SEAST SO, manufactured by Tokai Carbon Co., Ltd.), and 2 parts by mass of stearic acid were kneaded to produce a rubber composition A.

0.5 Part by mass of sulfur and 1.5 parts by mass of dipentamethylenethiuram tetrasulfide (trade name: NOC- CELER TRA, manufactured by Ouchi Shinko Chemical Industrial Co., Ltd.) were added to the rubber composition A obtained in the foregoing, and the mixture was kneaded with an open roll to produce a rubber composition B.

The rubber composition B was loaded into a sheet die having a thickness of 0.5 mm, and was vulcanized with a hot press at 160° C. for 15 minutes. Next, a rubber sheet removed from the die was vulcanized in an oven at 160° C. for 1 hour to produce a rubber composition 1.

Examples 10 and 11

Rubber compositions 2 and 3 were each produced by the same method as that of Example 7 except that in Example 7, the compound (4) was changed to a compound shown in Table 1, Comparative Example 1

Production of Comparative Resin Composition 1
A comparative resin composition 1 was produced by the same production method as that of Example 1 except that in Example 1, the compound (4) was not used.

Comparative Examples 2 to 5

Production of Comparative Resin Compositions 2 to 5
Comparative resin compositions 2 to 5 were each produced by the same production method as that of Example 1 except that in Example 1, the compound (4) was changed to any one of the following comparative compounds (1) to (4).

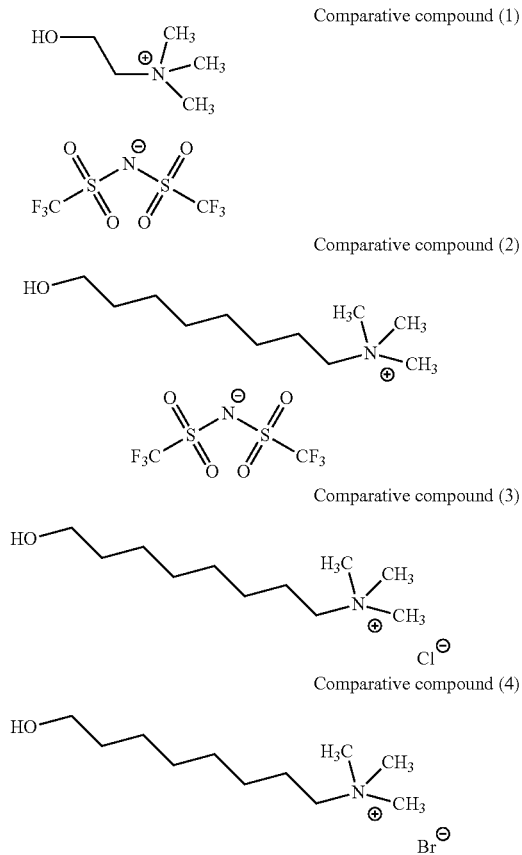

Bleeding Test Evaluation

The urethane resin compositions 1 to 8, the rubber compositions 1 to 3, and the comparative resin compositions 1 to 5 were each brought into abutment with a polyethylene terephthalate (PET) sheet, and the resultant was left at rest under an environment having a temperature of 40° C. and a humidity of 95% R.H. for 1 week. A portion in which the composition abutted with the surface of the PET sheet was observed with an optical microscope (VHX-500 manufactured by Keyence Corporation) (at a magnification of 10).

An evaluation was performed as described below, and when the result was B or higher, it was judged that no influence of bleeding was present. The results of the evaluation are shown in Table 1.

A: No bleeding product is observed in the abutting portion.
B: Slight haze is observed in part of the abutting portion.
C: Slight haze is observed in the entire surface of the abutting portion.
D: A bleeding product is remarkably observed in the entire surface of the abutting portion.

<Evaluation for Electroconductivity Change>

The outline of a machine for measuring the current values of the compositions is illustrated in FIGURE.

A sample (resin composition) 2 having a thickness of 0.5 mm was brought into abutment with a plate electrode 1, and a cylindrical electrode 4 having a guide ring 3 and having a diameter of 1 cm. Next, a direct current of 50 μA was applied from a power source 5 under an environment having a temperature of 23° C. and a humidity of 50% R.H. Two seconds after the application of the current, a voltage applied from the power source 5 to a resistance 6 was measured with a voltmeter 7 for 3 seconds, and the initial volume resistivity ($\Omega \cdot cm$) of the sample 2 was calculated from a time-averaged voltage.

The current of 50 μA was further applied for 10 Minutes. After that, the voltage applied from the power source 5 to the resistance 6 was measured with the voltmeter for 3 seconds, and the volume resistivity ($\Omega \cdot cm$) of the sample 2 after a Lapse of 10 minutes was calculated from a time-averaged voltage. The ratio of the volume resistivity after a lapse of 10 minutes to the initial volume resistivity was defined as an electroconductivity change ratio.

When a value for the electroconductivity change ratio was less than 2.0, it was judged that the composition was excellent in electroconductivity.

A: The electroconductivity change ratio is less than 1.5 (extremely excellent in electroconductivity).
B: The electroconductivity change ratio is 1.5 or more and less than 2.0 (excellent in electroconductivity).
C: The electroconductivity change ratio is 2.0 or more (poor in electroconductivity).

The results of Examples 1 to 11 and Comparative Examples 1 to 5 described above are shown in Table 1.

TABLE 1

| | Used anion compound | Compound | Used number of parts of compound | Used resin | Bleeding evaluation | Initial volume resistivity (Ω·cm) | Electroconductivity change ratio | Evaluation for electroconductivity change |
|---|---|---|---|---|---|---|---|---|
| Example 1 | Anion compound (2) | Compound (4) | 2 | Urethane resin composition 1 | A | 5.3E+07 | 1.29 | A |
| Example 2 | Anion compound (2) | Compound (4) | 10 | Urethane resin composition 2 | A | 1.1E+07 | 1.66 | B |
| Example 3 | Anion compound (2) | Compound (4) | 25 | Urethane resin composition 3 | B | 7.3E+06 | 1.85 | B |
| Example 4 | Anion compound (7) | Compound (8) | 2 | Urethane resin composition 4 | A | 6.6E+07 | 1.20 | A |
| Example 5 | Anion compound (5) | Compound (16) | 2 | Urethane resin composition 5 | A | 7.1E+07 | 1.32 | A |
| Example 6 | Anion compound (1) | Compound (17) | 2 | Urethane resin composition 6 | A | 4.9E+07 | 1.28 | A |
| Example 7 | Anion compound (2) | Compound (4) | 2 | Rubber composition 1 | B | 3.3E+07 | 1.70 | B |
| Example 8 | Anion compound (2) | Compound (18) | 2 | Urethane resin composition 7 | A | 3.5E+07 | 1.39 | A |
| Example 9 | Anion compound (2) | Compound (19) | 2 | Urethane resin composition 8 | A | 2.1E+07 | 1.44 | A |
| Example 10 | Anion compound (2) | Compound (18) | 2 | Rubber composition 2 | B | 2.3E+07 | 1.81 | B |
| Example 11 | Anion compound (2) | Compound (19) | 2 | Rubber composition 3 | B | 1.2E+07 | 1.93 | B |
| Comparative Example 1 | — | Not added | — | Comparative resin composition 1 | — | 8.1E+08 | — | — |
| Comparative Example 2 | — | Comparative compound (1) | 2 | Comparative resin composition 2 | C | 3.7E+07 | 2.51 | C |
| Comparative Example 3 | — | Comparative compound (2) | 2 | Comparative resin composition 3 | C | 6.2E+07 | 3.93 | C |
| Comparative Example 4 | — | Comparative compound (3) | 2 | Comparative resin composition 4 | D | 5.1E+07 | 4.01 | C |
| Comparative Example 5 | — | Comparative compound (4) | 2 | Comparative resin composition 5 | D | 5.5E+07 | 4.21 | C |

As is apparent from Table 1, a resin composition using the hydroxy compound according to the present invention was excellent in electroconductivity as compared with the case where no compound was added and a resin composition produced by using a comparative compound.

Further, it was found that the resin compositions according to Examples 1 to 6, 8, and 9 each obtained by bonding the hydroxy compound according to the present invention to a polymer were each suppressed in bleeding of the ion conducting agent and suppressed in electroconductivity change well.

According to the present invention, a hydroxy compound and an ion conducting agent each having excellent electroconductivity can be obtained. The use of the hydroxy compound provides an electroconductive resin composition excellent in electroconductivity. Accordingly, the composition can find use in, for example, precision instruments such as a liquid crystal display and an optical lens, automobile parts, substrates for magnetic recording media such as an optical disk, protective films for semiconductor materials and the like, paints, and adhesives.

While the present invention has been described with reference to exemplary embodiments, it is to be understood that the invention is not limited to the disclosed exemplary embodiments. The scope of the following claims to be accorded the broadest interpretation so as to encompass all such modifications and equivalent structures and functions.

This application claims the benefit of Japanese Patent Application No. 2014-101639, filed May 15, 2014, and Japanese Patent Application No. 2015-080045, filed Apr. 9, 2015 which are hereby incorporated by reference herein in their entirety.

What is claimed is:

1. A hydroxy compound having an anion species and a cation species, the anion species having a structure of

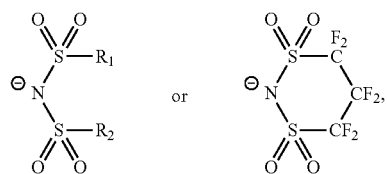

wherein each of $R_1$ and $R_2$ is, independently, a fluorine atom or a fluoroalkyl group having 1 to 8 carbon atoms; and the cation species having a structure of general formula (1):

General formula (1)

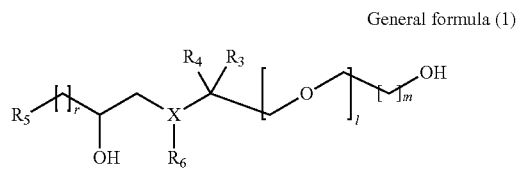

wherein, in the general formula (1):
r is an integer of 1 to 20,
m is an integer of 0 to 20,
l is an integer of 0 to 20, with a proviso that, when l is 0, m is an integer of 1 to 20, and when l is an integer of 1 to 20, m is 1;

X is a nitrogen atom or —N⁺(—R₁₄)—, wherein R₁₄ is an alkyl group having 1 to 4 carbon atoms;

each of R₃ and R₄ is, independently, a hydrogen atom or an alkyl group having 1 to 20 carbon atoms;

R₅ is a hydroxyl group, an amino group, or a group having a structure of general formula (2):

General formula (2)

wherein, in the general formula (2), each of R₇, R₈, and R₉ is, independently, an alkyl group having 1 to 20 carbon atoms, and * is a bonding site;

R₆ is an alkyl group having 1 to 4 carbon atoms or a group having a structure of general formula (3):

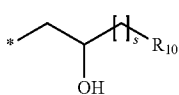

General formula (3)

wherein, in the general formula (3), s is an integer of 1 to 20, * is a bonding site, and R₁₀ is a hydroxyl group, an amino group, or a group having a structure of general formula (4):

General formula (4)

wherein, in the general formula (4), each of R₁₁ R₁₂, and R₁₃ is, independently, an alkyl group having 1 to 20 carbon atoms, and * is a bonding site; and wherein when X is a nitrogen atom, at least one of condition (i) and condition (ii) is satisfied:

(i) R₅ is the group having the structure of the general formula (2); and (ii) R₆ is the group having the structure of the general formula (3), and R₁₀ in the general formula (3) is the group having the structure of the general formula (4).

2. The hydroxy compound according to claim 1, wherein, in the general formula (1), each of R₁ and R₂ is a perfluoroalkyl group having 1 to 8 carbon atoms.

3. The hydroxy compound according to claim 1, wherein, in the general formula (1), each of R₁ and R₂ is a trifluoromethyl group.

4. The hydroxy compound according to claim 1, wherein, in the general formula (1), l is 0 and m is an integer of 1 to 20.

5. An ion conducting agent, comprising a hydroxy compound, wherein the hydroxy compound has an anion species and a cation species, the anion species having a structure of

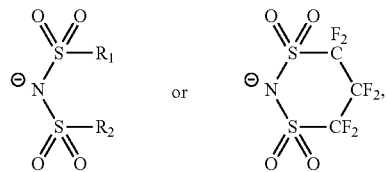 or 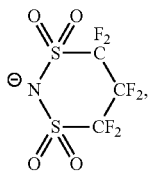

wherein each of R₁ and R₂ is, independently, a fluorine atom or a fluoroalkyl group having 1 to 8 carbon atoms; and the cation species having a structure of general formula (1):

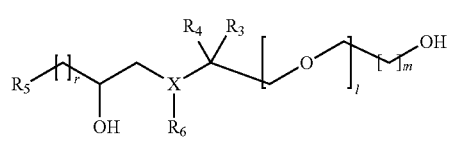

General formula (1)

wherein, in the general formula (1):
r is an integer of 1 to 20,
m is an integer of 0 to 20,
l is an integer of 0 to 20, with a proviso that, when l is 0, m is an integer of 1 to 20, and when l is an integer of 1 to 20, m is 1;
X is a nitrogen atom or —N⁺(—R₁₄)—, wherein R₁₄ is an alkyl group having 1 to 4 carbon atoms;
each of R₃ and R₄ is, independently, a hydrogen atom or an alkyl group having 1 to 20 carbon atoms;
R₅ is a hydroxyl group, an amino group, or a group having a structure of general formula (2):

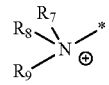

General formula (2)

wherein, in the general formula (2), each of R₇, R₈, and R₉ is, independently, an alkyl group having 1 to 20 carbon atoms, and * is a bonding site;

R₆ is an alkyl group having 1 to 4 carbon atoms or a group having a structure of general formula (3):

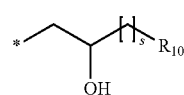

General formula (3)

wherein, in the general formula (3), s is an integer of 1 to 20, * is a bonding site, and R₁₀ is a hydroxyl group, an amino group, or a group having a structure of general formula (4):

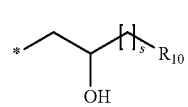

General formula (3)

wherein, in the general formula (4), each of $R_{11}$, $R_{12}$, and $R_{13}$ is, independently, an alkyl group having 1 to 20 carbon atoms, and * is a bonding site; and wherein when X is a nitrogen atom, at least one of condition (i) and condition (ii) is satisfied:

(i) $R_5$ is the group having the structure of the general formula (2); and (ii) $R_6$ is the group having the structure of the general formula (3), and $R_{10}$ in the general formula (3) is the group having the structure of the general formula (4).

6. An electroconductive resin composition, comprising a hydroxy compound, wherein the hydroxy compound has an anion species and a cation species, the anion species having a structure of

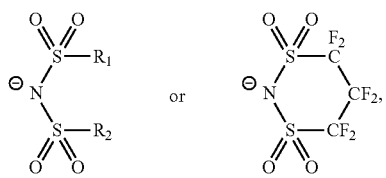

or wherein each of $R_1$ and $R_2$ is, independently, a fluorine atom or a fluoroalkyl group having 1 to 8 carbon atoms; and the cation species having a structure of general formula (1):

General formula (1)

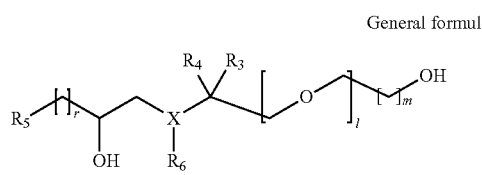

wherein, in the general formula (1):

r is an integer of 1 to 20, m is an integer of 0 to 20, l is an integer of 0 to 20, with a proviso that, when l is 0, m is an integer of 1 to 20, and when l is an integer of 1 to 20, m is 1;

X is a nitrogen atom or —N$^+$(—R$_{14}$)—, wherein $R_{14}$ is an alkyl group having 1 to 4 carbon atoms;

each of $R_3$ and $R_4$ is, independently, a hydrogen atom or an alkyl group having 1 to 20 carbon atoms;

$R_5$ is a hydroxyl group, an amino group, or a group having a structure of general formula (2):

General formula (2)

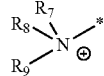

wherein, in the general formula (2), each of $R_7$, $R_8$, and $R_9$ is, independently, an alkyl group having 1 to 20 carbon atoms, and * is a bonding site;

$R_6$ is an alkyl group having 1 to 4 carbon atoms or a group having a structure of general formula (3):

General formula (3)

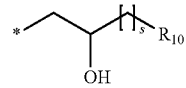

wherein, in the general formula (3), s is an integer of 1 to 20, * is a bonding site, and $R_{10}$ is a hydroxyl group, an amino group, or a group having a structure of general formula (4):

General formula (4)

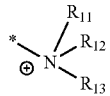

wherein, in the general formula (4), each of $R_{11}$, $R_{12}$, and $R_{13}$ is, independently, an alkyl group having 1 to 20 carbon atoms, and * is a bonding site; and wherein when X is a nitrogen atom, at least one of condition (i) and condition (ii) is satisfied:

(i) $R_5$ is the group having the structure of the general formula (2); and (ii) $R_6$ is the group having the structure of the general formula (3), and $R_{10}$ in the general formula (3) is the group having the structure of the general formula (4).

* * * * *